United States Patent [19]

Loeb

[11] 4,448,188

[45] May 15, 1984

[54] METHOD FOR PROVIDING AN OXYGEN BEARING LIQUID TO A BLOOD VESSEL FOR THE PERFORMANCE OF A MEDICAL PROCEDURE

[75] Inventor: Marvin P. Loeb, Chicago, Ill.

[73] Assignee: Laserscope, Inc., Arlington Heights, Ill.

[21] Appl. No.: 349,718

[22] Filed: Feb. 18, 1982

[51] Int. Cl.³ .............................................. A61B 1/06
[52] U.S. Cl. ..................................... 128/6; 128/303.1; 128/395; 604/96
[58] Field of Search ........... 128/1 R, 6, 303.1, 303.11, 128/303.12, 325, 344, 346, 395; 604/96

[56] References Cited

U.S. PATENT DOCUMENTS

| | | | |
|---|---|---|---|
| 3,516,408 | 6/1970 | Montanti | 604/96 X |
| 3,911,138 | 10/1975 | Clark, Jr. | 424/352 |
| 3,989,843 | 11/1976 | Chabert et al. | 424/352 X |
| 4,105,798 | 8/1978 | Moore et al. | 424/352 |
| 4,175,545 | 11/1979 | Termanini | 128/6 X |
| 4,204,528 | 5/1980 | Termanini | 128/6 |
| 4,207,874 | 6/1980 | Choy | 128/6 |
| 4,213,461 | 7/1980 | Pevsner | 604/96 |
| 4,224,929 | 9/1980 | Furihata | 128/6 X |
| 4,263,917 | 4/1981 | Moss | 128/344 X |
| 4,289,499 | 9/1981 | Clark, Jr. et al. | 424/352 X |

OTHER PUBLICATIONS

Bing; O. H. L. et al., "Isolated Cardiac Muscle Performance During Fluorocarbon Immersion and Effects of Metabolic Blockade, " *Proc. Soc. Exp. Bio. Med.* 158:561–564 (1978).

"Proceedings of the Fourth International Symposium on Perfluorocarbon Blood Substitutes, " *Excepta Medica* (1979).

Grady; Denise "The Artery Zapper", *Discover* (Dec. 1982) pp. 36–40.

*Primary Examiner*—Kyle L. Howell
*Assistant Examiner*—Christine A. Fukushima

[57] ABSTRACT

A method for providing an oxygen bearing liquid to a blood vessel during the performance of a medical procedure is disclosed. In one preferred embodiment the blood flow is temporarily occluded, a substantially clear oxygen bearing liquid is introduced into the blood vessel and the inside of the blood vessel is inspected through a viewing system and treated with laser irradiation.

30 Claims, 5 Drawing Figures

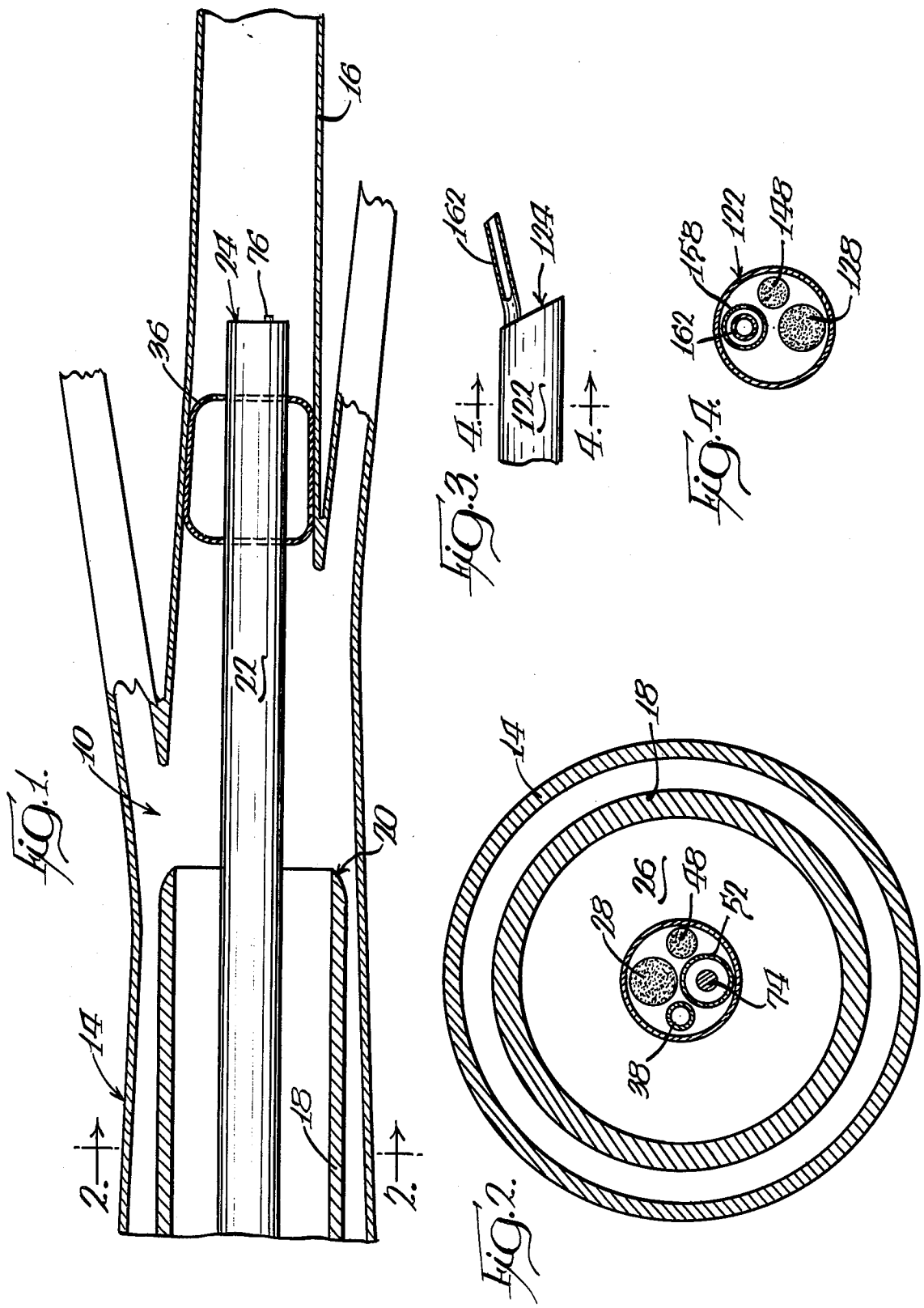

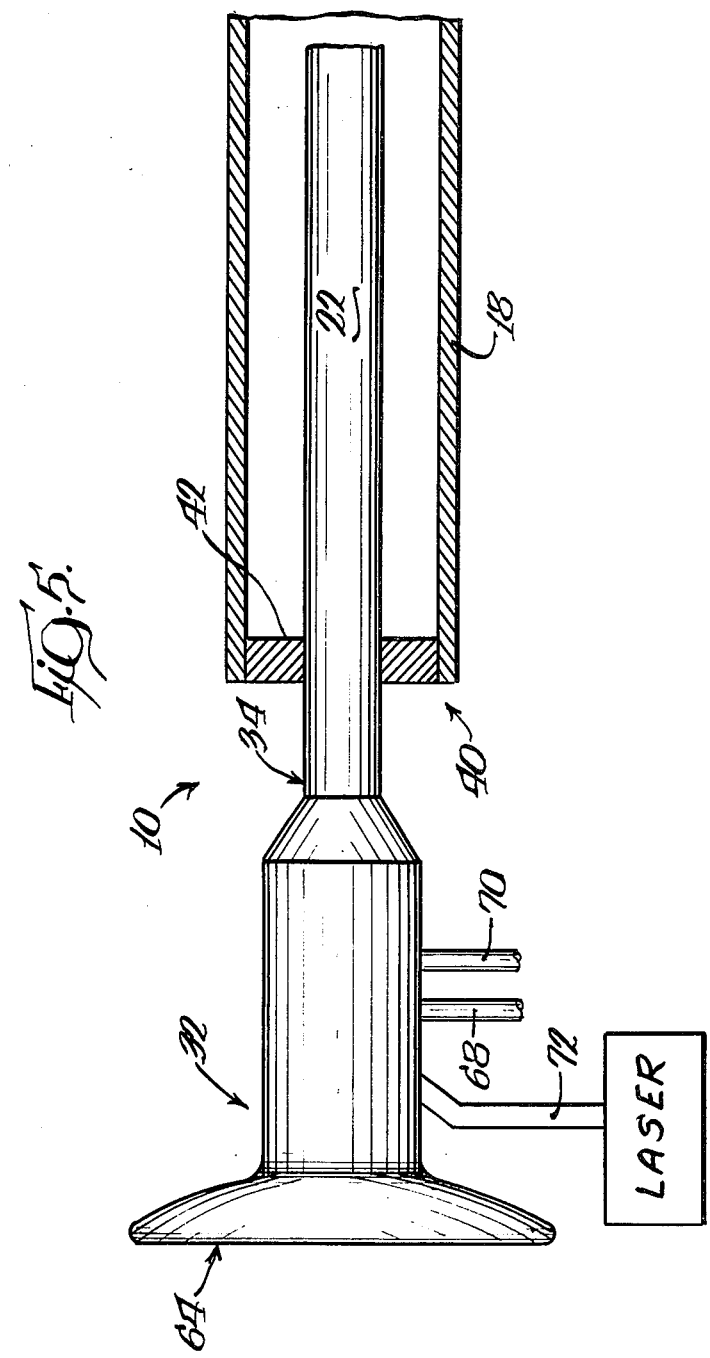

METHOD FOR PROVIDING AN OXYGEN BEARING LIQUID TO A BLOOD VESSEL FOR THE PERFORMANCE OF A MEDICAL PROCEDURE

TECHNICAL FIELD OF INVENTION

This invention relates to the performance of a medical procedure within a blood vessel and more particularly to a method for providing an oxygen bearing liquid to the blood vessel during the procedure.

BACKGROUND OF THE INVENTION

Cardiovascular diseases continue to be an ongoing problem, particularly in an advanced society. Particularly serious is the progressive blockage of a blood vessel by the collection or deposit of materials such as arteriosclerotic plaque and thrombosis. It has been estimated that every year more than one half million Americans die from coronary disease. Another 3.5 million are believed to suffer some degree of incapacitation because of coronary disease.

Various devices and methods have been developed in the past in an attempt to deal with the problems of cardiovascular diseases. One method has been to physically force a blood vessel open. A balloon is positioned within a plaque constricted part of a blood vessel and inflated with the hope that the plaque will be compressed within the walls of the blood vessel and the vessel widened. This process, however, has only met with limited success and is only applicable to certain cases. Various tissue collecting devices have in the past been inserted into lumens to either remove material causing constrictions, or to collect material for biopsy. Other devices have included laser light carrying fibers to direct laser irradiation into the lumen.

All of these devices have their various shortcomings. One common shortcoming is that it is difficult to view a site within a blood vessel while blood is present. To facilitate viewing, it is necessary to occlude the blood flow and flush the blood vessel with a clear fluid such as saline. Even before the flow is fully occluded, the presence of such a device in a blood vessel alone can reduce the blood flow enough to have a detrimental effect upon tissue downstream of the device.

While occluding the blood flow can have little detrimental effect in areas of the body having an extensive cross network of blood vessels (i.e. anastomoses) which otherwise supply the tissue downstream, other areas of the body have few anastomoses. One area of the body having few anastomoses between larger arteries is the vascular network surrounding the heart.

The occlusion of a coronary artery stops the flow of blood and deprives the heart tissue of oxygen downstream of the occlusion. After about fifteen seconds, the cardiac muscle downstream of the occlusion begins to suffer damage and eventually dies. Such an occlusion in nature is known as a myocardial infarction and, if one of the larger coronary arteries is blocked, there can be immediate death.

The prior devices and methods cannot be used in such tissue where the blood flow must be stopped or occluded for any significant length of time. Accordingly, it would be desirable to provide a method which avoids the shortcomings of the prior art and provides an effective means for performing a medical procedure within a blood vessel while providing an adequate oxygen supply to the surrounding tissue. The present invention meets this desire.

SUMMARY OF THE INVENTION

The present invention is a method for obtaining access to a site in a blood vessel to perform a medical procedure while providing an adequate supply of oxygen to the tissue downstream of the medical procedure site. The medical procedure can be the visual inspection of the blood vessel, the collection of a biopsy tissue sample or the treatment of a blockage or deposit in the blood vessel.

The method is generally performed by temporarily occluding a blood vessel upstream of the operative site with a removable flow occluding means such as a balloon and introducing a physiologically compatible, oxygen bearing liquid downstream of the flow occluding means. This liquid bears sufficient available oxygen to maintain the viability of the tissue downstream of the flow obstruction means. The oxygen bearing liquid can be blood such as the patient's own blood. Preferably, the oxygen bearing liquid is a substantially clear emulsion of a perfluorocarbon.

In the event the oxygen-bearing liquid is not sufficiently clear to permit viewing or laser beam passage without material attenuation, a substantially clear flushing fluid can be temporarily introduced downstream of the vessel occluding means during at least part of the medical procedure to permit viewing of a desired site with a fiber optic viewing system, the use of operative means such as a tissue collector or laser irradiation.

The method of the present invention can be practiced with a microcatheter device which includes a means for occluding the vessel, a fluid passageway for introducing the oxygen bearing liquid and flushing fluid downstream of the occlusion. The microcatheter device can also be provided with one or more of a fiber optic viewing system, a laser light transmitting fiber, and biopsy tissue collection means.

Numerous other advantages and features of the present invention become readily apparent from the following detailed description of the invention, the accompanying examples, the drawings and the appended claims.

BRIEF DESCRIPTION OF THE DRAWINGS

FIG. 1 is a side elevational view, partly in section, showing the distal end of a microcatheter device suitable for practicing the present invention located within a blood vessel network;

FIG. 2 is a cross-sectional view of the microcatheter device taken generally along plane 2—2 of FIG. 1;

FIG. 3 is a fragmentary view of the distal end of an alternative microcatheter device;

FIG. 4 is a cross-sectional view taken generally along plane 4—4 of FIG. 3 showing the internal structure of the alternative microcatheter device of FIG. 3; and FIG. 5 is a side elevational view, partly in section, showing the proximal end of the microcatheter device of FIG. 1.

DESCRIPTION OF THE PREFERRED EMBODIMENTS

While this invention is susceptible of embodiment in many different forms, there are shown in the drawings and will be described in detail, preferred embodiments of the invention. It should be understood, however, that the present disclosure is to be considered as an exemplification of the principles of the invention and is not intended to limit the invention to the embodiments illustrated.

The precise shapes and sizes of the components described are not essential to the invention unless otherwise indicated. For ease of description the microcatheter device suitable for practicing this invention is shown as operating in a horizontal position. It will be understood, however, that this invention may be practiced in any appropriate orientation.

This invention relates to a method for obtaining access to a site in a blood vessel for the performance of a medical procedure. Many types of medical procedures can be performed within a blood vessel using the method of the present invention. Such procedures include the visual inspection of the blood vessel from within, the collection of tissue as for a biopsy, infusion of drugs, and laser irradiation of the surface of the blood vessel for such purposes as the removal of a plaque deposit.

To perform such medical procedures it is necessary to occlude the flow of blood upstream from the site. Unless the procedure can be performed in a matter of seconds, such an occlusion can be detrimental or fatal to tissues downstream which lack an alternative source of oxygen. For example, the two coronary arteries, the right and the left, have few anastomoses within their branches which would provide an alternative arterial blood flow to tissues downstream of an occlusion. Thus, it is necessary to provide these tissues with an alternative source of oxygen.

While the present invention is suited for use in blood vessels located anywhere in a human body, as an example, the present invention will be described as being used in a coronary artery.

The method of the present invention generally comprises the steps of temporarily occluding the blood vessel upstream of the site, introducing downstream of the occlusion an oxygen bearing liquid, and positioning operative means adjacent the site for performing the medical procedure. Flow occluding means such as an inflatable balloon is introduced into the blood vessel upstream of the site to temporarily occlude the flow of blood. The oxygen bearing liquid can then be introduced downstream of the occlusion by a tube which passes around or through the occluding means, e.g. the balloon may be located circumferentially about the tube.

The oxygen bearing liquid is a physiologically compatible liquid bearing sufficient available oxygen to maintain the viability of tissue downstream of the flow occlusion. The term "sufficient available oxygen to maintain the viability of tissue" is to be understood as meaning tha the liquid can release enough oxygen to keep the tissue from suffering irreparable damage during the procedure. In a typical adult, each of the two main coronary arteries generally maintains a blood flow rate of 40 to 60 cubic centimeters per minute. To avoid damage to tissue downstreaam of the occlusion, a minimum flow rate of 20 to 30 cubic centimeters of blood should be maintained, or a flow rate of a liquid other than blood providing a comparable oxygen content. If the oxygen-bearing liquid is to flow through a relatively small diameter tube, substantial pressure will be required to produce the desired flow rate. Sufficient available oxygen to maintain the viability of the tissue can be provided by a relatively small volume of a liquid having a relatively high percentage of available oxygen, or by a larger volume or flow of a liquid having a relatively lower percentage of available oxygen. Preferred compositions of the oxygen bearing liquid are described in more detail below.

The operative means can include a viewing system, tissue collection means, drug infusion means and means for emanating laser irradiation within the blood vessel. These operative means can be used alone or together to accomplish the desired medical procedure.

Where the oxygen-bearing liquid is not adequately transparent to visible light or laser energy a substantially clear flushing fluid (i.e., a physiologically tolerable liquid or gas) is introduced into the blood vessel downstream of the occlusion during at least part of the medical procedure. This permits viewing of the site with a viewing system as well as transmitting laser irradiation within the vessel to the site.

The nature of the flushing fluid selected in any given case depends on the surgical procedure to be performed. For example, some forms of laser energy are absorbed more in certain liquid media than in certain gaseous media.

By "substantially clear" it is to be understood that the transparency of the liquid or gas is sufficient to permit viewing within the blood vessel by use of a viewing system or the use of a laser.

This flushing can generally be accomplished by several techniques. Where the oxygen-bearing liquid is blood the flushing fluid can be a substantially clear oxygen-bearing liquid or a substantially clear non-oxygen-bearing liquid or gas. The oxygen-bearing liquid can be an oxygenated aqueous perfluorocarbon emulsion as will be discussed in greater detail hereinbelow. The non-oxygen-bearing fluid can be a liquid such as physiological saline or it can be a biocompatible gas such as carbon dioxide or the like.

Where the oxygen-bearing liquid is a blood substitute lacking in the desired transparency to visible light or the laser energy to be used, the flushing fluid can likewise be a substantially clear, physiologically tolerable oxygen-bearing liquid or a non-oxygen-bearing liquid or gas as described in the immediately preceding paragraph.

In addition, more than one flushing fluid can be used in sequence during a medical procedure in order to maximize the desired transparency to a particular laser wavelength. For instance, various oxygenated perfluorocarbon emulsions can be introduced in sequence, an oxygenated perfluorocarbon emulsion can be followed by physiological saline, an oxygenated perfluorocarbon emulsion can be followed by injection of a predetermined quantity of carbon dioxide which temporarily displaces liquid present at the site, etc. Furthermore, to limit the total quantity of auxiliary liquids or gases that are administered, the patient's own blood or donor blood may be intermittently administered during perods when viewing of or use of a laser are not necessary. Alternatively, the flushing fluid may include blood, e.g., patient's own blood diluted with a clear, physiologically compatible liquid to provide the desired transparency during viewing or laser use.

The amount of clear flushing fluid to be introduced depends on the opaqueness and volume of the oxygen-bearing liquid needed to be displaced for clear viewing or the use of a laser or biopsy device.

After all or part of the medical procedure has been performed, the flushing fluid can be replaced with more oxygen bearing liquid or the flow occlusion means removed to permit blood flow. In either case, the oxygen available to the tissue is only interrupted for a relatively brief period, if at all.

During positioning and removal of the microcatheter device when the occlusion means is not being used, the blood flow around the device to the tissue downstream can be supplemented by the oxygen bearing liquid. Thus the detrimental effects that could be caused by the partial or total interruption of blood flow while a device is being located in a blood vessel are avoided. A radio-opaque dye or a chemotherapeutic agent such as streptokinase can also be infused with the oxygen bearing liquid, if desired.

In the preferred embodiment, the oxygen bearing liquid is a water based emulsion of a perfluorocarbon of the type which have been used and proposed as a synthetic blood. Such an emulsion can be clear and, unlike blood, is not likely damaged by being pumped into the blood vessel. Examples of typical perfluorocarbons which have been tested for their ability to serve as synthetic blood components include perfluorodecalin; perfluoro(1-methyldecalin); perfluorodimethyldecalin; perfluoromethylcyclohexane; perfluorotributylamine; perfluoro(1,3-dimethylcyclohexane); perfluoroadamantane; perfluoromethyladamantane; perfluorodecahydro-1-methylnaphthalene; perfluorodimethyladamantane; perfluoro-n-pentane; perfluorohexane; perfluoroheptane; perfluorobicyclo[4.3.0]nonane; perfluoro (1,8 diisopropoxyoctane); perfluorotetrahydrodicyclopentadiene; perfluoro-7-methylbicyclo[4.3.0]nonane; perfluorobicyclo[5.3.0]decane; perfluoro-p-menthane; perfluorotetramethylcyclohexane; perfluoro-n-butylcyclohexane; perfluorotrimethylbicyclo[3.3.1]nonane; and the like.

Other perfluorocarbons useful as synthetic blood components include, in addition to the above, substituted perfluorocarbons such as other halogen substituted hydrocarbon derivatives including mono- or di-bromo, iodo, etc., perfluorocarbons, specifically perfluoroctyl bromide. Other heteroperfluorocarbons include perfluoro cyclic amines, and perfluoro cyclic ethers, as well as mixtures of the same with the aforesaid perfluoro paraffinic or cyclic hydrocarbons.

Generally it has been found that as synthetic blood components, those perfluorocarbons having 9 to 12 carbon atoms are preferred. Of the foregoing grouping the cyclic perfluorocarbons are more preferred. Such fluorocarbons are described in U.S. Pat. No. 4,289,499 to Clark et al.

The perfluorocarbon chosen should have a vapor pressure below about 40 to 50 torr at 37° C. to prevent high evaporation and problems similar to the bends. On the other hand, the vapor pressure should not be so low that the perfluorocarbon remains in the body for an undesirably long time period. A preferred vapor pressure range for the perfluorocarbon is about 20 to 40 torr at 37° C. Generally the perfluorocarbon is eliminated from the body by transfer out through the skin and lungs.

Because perfluorocarbons are not directly compatible with blood, it is necessary that they be prepared as an oil in water emulsion. It is preferred that a 10 to 20 percent perfluorocarbon emulsion be prepared with a particle size below about 0.1 micrometers thus providing a substantially clear oxygen bearing liquid. The perfluorocarbon can be emulsified in water or saline solutions with mechanical or ultrasonic homogenization or by the use of non-ionic emulsifiers, preferably polyfluorinated emulsifiers.

For mechanical and sonic homogenization, a 10 percent fluorocarbon emulsion is prepared by placing 10 millimeters of fluorocarbon liquid into a 100 milliliter cylinder and then adding 90 milliliters of aqueous phase. This aqueous phase can be water alone or can contain desired salts and glucose for physiological purposes. The aqueous phase also includes a non-ionic surfactant or emulsifying agent, for example, a polyoxyethylenepolyoxypropylene copolymer having a molecular weight of about 8200 (Pluronic F68, available from BASF Wyandotte Chemical Corp. of Wyandotte, Mich.). About 1 to 20 volume percent of Pluronic F68 surfactant can be used. Because of the potential toxicity of the Pluronic F68, it is preferred that it be charcoal treated.

The resulting mixture is then placed in a blender for less than a minute to form a coarse emulsion and suspend the perfluorocarbon in the aqueous phase. The coarse emulsion can then be further emulsified in two preferred ways, the use of a homogenizer, e.g., a Gaulin model 15M homogenizer or the use of a sonicator e.g., a Branson model LS-75. After homogenization or sonication, the emulsions are centrifuged to remove the population of large particles. An ion exchange procedure is then used to remove fluorine ions that may have been released during the homogenization or sonication.

It is preferred that the produced emulsion have a average particle size less than about 0.1 to 0.2 micrometers not only because such an emulsion is a substantially clear liquid, but also because the resulting emulsion is more stable than emulsions having larger particle sizes. To prepare such a smaller particle size, it has been found that about 5 volume percent of Pluronic F68 should be added to produce a 10 volume percent fluorocarbon emulsion. The preparation of perfluorocarbon emulsions by mechanical and sonic methods are well-known in the art. See generally U.S. Pat. Nos. 3,911,138 to Clark, and 4,105,798 to Moore et al.

Aqueous emulsions of perfluorocarbons can also be prepared by using at least one predominantly lipohilic polyfluorinated emulsifier together with at least one predominantly hydrophilic polyfluorinated emulsifier. The perfluorocarbon is mixed together with the two emulsifiers in a water or aqueous solution containing desired salts and glucose for physiological purposes. The resulting mixture is then heated with stirring to about 70 C. or higher and cooled with continued stirring until a transparent emulsion is formed. This avoids some of the difficulties of mechanical or ultrasonic homogenization such as the production of toxic fluorine. For further details on the mixing procedure, as well as emulsifying agents, reference is made to U.S. Pat. No. 3,989,843 to Chabert et al.

As an example, one perfluorocarbon which can be prepared into a clear emulsion by the above method is perfluorotributylamine. Into a glass reactor are placed 80 milliliters of distilled water and 20 milliliters of perfluorotributylamine. Also placed in glass reactor are 4.1 grams of a highly hydrophilic surfactant mixture of polyethoxylated 2-perfluorohexyl-ethyl alcohols having the weight-average composition:

$C_6F_{13}(C_2H_4O)_{12.3}H$ and 2.7 grams of a low hydrophilic surfactant mixture having the weight-average composition:

$C_6F_{13}(C_2H_4O)_{3.8}H$ composed of six surfactants:

or

distributed in the following manner:

| s | n | Percent by weight |
|---|---|---|
| 1 | 0 | 7 |
| 2 | 1 | 6 |
| 3 | 2 | 7 |
| 4 | 3 | 65 |
| 5 | 4 | 13 |
| 6 | 5 | 2 |

The compositions are then mixed and heated to 70 degrees C. and allowed to cool slowly with gentle agitation with the aid of a magnetic stirer. A stable transparent emulsion is obtained in the temperature range of 30 to 42 degrees C. While the temperature is maintained in this range, the emulsion is filtered through a Millipore filter of 0.22 micrometer pore size.

As stated above, about a about 10 to 20 volume percent perfluorocarbon emulsion is preferred. As an example, two perfluorocarbons which have found extensive use as a component in synthetic blood compositions because of their relatively high transpiration rate are perfluorodecalin and perfluorotributylamine. A substantially clear emulsion of perfluorodecalin or perfluorotributylamine can be produced by the procedures described above. For further information regarding the production, testing, and use of perfluorocarbon emulsions, reference is made to: *Proceedings of The Fourth International Symposium on Perfluorocarbon Blood Substitutes* published by Excerpta Medica (1979).

A perfluorocarbon emulsion in water can be used without substantial adverse effect to cardiac muscle tissue. See, Bing et al., "Isolated Cardiac Muscle Performance During Fluorocarbon Immersion and Its Effects of Metabolic Blockade", Proc. Soc. Exp. Bio. Med., 158:561–564 (1978). It is preferred, however, that a perfluorocarbon solution be made with a solution containing compounds to simulate the properties of whole blood. One such composition is shown below.

| CONSTITUENT | 100 ml Basis |
|---|---|
| Perfluorochemical | 11.0–13.0 ml. |
| Pluronic F68 | 2.3–2.7 g |
| Hydroxyethyl starch | 2.5–3.2 g |
| Glucose | 0.1 g |
| NaCl | 54 mg |
| KCl | 32 mg |
| MgCl$_2$ | 7 mg |
| CaCl$_2$ | 10 mg |
| NaH$_2$PO$_4$ | 9.6 mg |
| Na$_2$CO$_3$ | q.s. To pH 7.44 |
| H$_2$O | q.s. To 100 ml |

Optimally, the oxygen bearing liquid is a substantially clear perfluorocarbon emulsion which is substantially isotonic with blood. Generally, a perfluorocarbon emulsion can normally carry 7–15 milliliters of oxygen per 100 milliliters of emulsion. In comparison, normal blood generally contains about 20 milliliters of oxygen per 100 milliliters of blood. All of the foregoing solubilities are at 25 C. and 760 millimeters of mercury. At rest, approximately 250 milliliters of blood flow through both of the two main coronary arteries of the average adult heart. With the oxygen solubility of perfluorocarbon emulsions, it is possible to supply the same amount of oxygen to one of the main coronary arteries with about 160 milliliters of emulsion per minute. Less emulsion is necessary to maintain the viability of the tissues where the blood flow to the tissues is only occluded for a short period of time.

Prior to its introduction into the blood vessel, the perfluorocarbon emulsion should be oxygenated. This can be accomplished by the use of artificial lung technology known to the art. One such expedient is to pass the perfluorocarbon emulsion through a membrane oxygenator having poly(tetrafluoroethylene) (Teflon) membranes. It is preferred to use a bubble oxygenator into which a mixture of 95 percent oxygen and 5 percent carbon dioxide is passed. A low level of carbon dioxide dissolved in a fluorocarbon is preferred because its presence, which is normal in arterial blood, aids in the muscle relaxation of the heart in between beats. Other preferred embodiments of the method are described in conjunction with the microcatheter device below.

An apparatus useful for practicing the present invention is shown in FIG. 1. A microcatheter device 10 is received within an arterial network including a larger artery 14 and a smaller artery 16 downstream. Other artery branches are also shown. The microcatheter device generally comprises an elongated flexible external guide tube 18 having a proximal end and a distal end 20, and an elongated flexible internal conduit 22 also having a proximal end and a distal end 24. The internal conduit 22 has a length greater than the length of the tube 18 and the conduit is mounted for movement substantially within space 26 (FIG. 2) defined by the tube with the distal end 24 of the conduit extendable beyond the distal end 20 of the tube.

The microcatheter device 10 also includes a viewing system, preferably fiberoptic, carried by the internal conduit 22 and substantially coterminous with the distal end 24 of the conduit. The fiberoptic viewing system generally includes a fiberoptic viewing bundle 28 (FIG. 2) which extends along the internal conduit 22 and an eyepiece arrangement included with handle 32 on the proximal end 34 of the internal conduit (FIG. 5).

The fiberoptic viewing system also includes means for supplying viewing light through the distal end 24 of the conduit 22. This can be accomplished by transmitting a light through the fiberoptic viewing bundle 28 or as shown in FIG. 2, by providing a separate light transmitting bundle 48. The use of a separate light transmitting bundle is preferred for sending a monochromatic light beam through the fiberoptic viewing bundle 28.

Referring again to FIGS. 1 and 2, flow occluding means such as balloon 36 is located circumferentially on the internal conduit 22 proximate the distal end 24 for stopping the flow of blood. After the distal end 24 of the internal conduit 22 has been positioned at a desired location within the blood vessel e.g., by being tracked by fluoroscopy, the balloon 36 is inflated by injecting a fluid such as saline or a gas such as carbon dioxide through channel 38 (FIG. 2). The channel 38 can either be defined by a separate tube within the internal conduit 22 as shown, or can be defined by the wall of internal conduit. To facilitate tracking by fluoroscopy the distal ends of the external tube 18 or internal conduit 22 can include a radiopaque material. After the internal conduit 22 has reached a desired location, the balloon 36 is inflated to fix its position and occlude the blood flow.

To introduce the oxygen bearing liquid and flushing fluid into the blood vessel the microcatheter device also includes a fluid passageway 52 carried by the internal conduit 22 and extending to the distal end 24 of the internal conduit. This permits the oxygen bearing fluid and/or flushing fluid to be introduced into the blood vessel downstream of the occlusion means.

An alternative design for the internal conduit is shown in FIGS. 3 and 4. The internal conduit 122 in this design also has a viewing fiberoptic bundle 128 and a light transmitting bundle 148. The conduit 122 also defines a duct 158 through which a hose 162 can be extended beyond the distal end 124 of the internal conduit. With this arrangement, the distal end 124 of the internal conduit 122 can be positioned adjacent the desired operation site, and the tube 162 extended until it contacts the desired tissue. A negative pressure is then introduced within the tube 162 and it is withdrawn, drawing with it the desired tissue. The process can be used to remove either an undesired obstruction within the blood vessel, or to acquire tissue for biopsy purposes.

Referring to FIG. 5, at the proximal end 40 of the external tube 18, a seal means such as collet 42 provides a seal between the external tube and the internal conduit 22 such that the internal conduit can be rotated and be moved axially with respect to the external tube. The viewing handle 32 includes an eyepiece 64 and internal coupling optics (not shown but well-known in the art) for viewing through the fiberoptic viewing bundle 28. A fluid inlet 70 is mounted on the handle 32 in fluid communication with the fluid passageway 52 to place it in communication with an oxygen bearing liquid and flushing fluid source. The handle 32 also includes a light source connection 68 for the light transmitting bundle 48. The handle 32 is also provided with a connecting fiber 72 for connecting the laser light transmitting fiber with a laser source.

Preferably, means are provided for emitting laser radiation from the distal end of the internal conduit. This can be by a separate laser light transmitting fiber 74 carried by the internal conduit 22. The fiber 74 preferably extends within the fluid passageway 52 so the fluid passes about the end of the fiber to prevent debris from collecting on the end. The laser light transmitting fiber 74 is preferably a single quartz glass fiber surrounded by a protective sheet. A replaceable transparent window 76 may be positioned on the distal end of the fiber 74 to protect the end of the fiber.

Preferably, the window is of glass or quartz and may include a lens to focus the laser light at a specific distance. The laser light should be emitted with respect to internal conduit 22 such that it appears approximately in the center of the viewing field of the fiberoptic viewing system. Should the window 76 become damaged, it may be replaced, avoiding the cost and necessity of replacing the entire laser light transmitting fiber 74.

The laser used may be any suitable laser such as a Ruby, Argon, or Neodymium-YAG (yttrium-aluminum-garnet) laser or the like. Preferably, a Neodymium-YAG (5320 Angstroms) laser is used. A second, lower level laser can also be coupled with the first laser to serve as a spotting laser.

The foregoing specification is intended as illustrative and is not to be taken as limiting. Still other variations within the spirit and scope of this invention are possible and will readily present themselves to those skilled in the art.

What is claimed is:

1. A method for obtaining access to a site in a blood vessel for the performance of a medical procedure, the method comprising the steps of:
    (a) temporarily occluding the blood vessel by introducing therein, upstream of the site, removable flow occluding means;
    (b) introducing downstream of the flow occluding means a physiologically compatible liquid, from an external source, bearing sufficient available oxygen to maintain the viability of tissue downstream of the flow obstruction means while the blood vessel is occluded; and
    (c) positioning operative means adjacent the site for performing the medical procedure.

2. The method of claim 1 wherein the oxygen bearing liquid is substantially clear.

3. The method of claim 1 wherein oxygen bearing liquid is a water based emulsion of a perfluorocarbon.

4. The method of claim 1 wherein the oxygen bearing liquid includes blood.

5. The method of claim 1 wherein the operative means includes a laser light transmitting fiber and the method includes introducing a substantially clear flushing fluid into the blood vessel during at least part of the performance of the medical procedure.

6. The method of claim 1 wherein a substantially clear flushing fluid is introduced into the blood vessel downstream of the flow occluding means during at least part of the performance of the medical procedure.

7. The method of claim 6 wherein the flushing fluid is saline.

8. The method of claim 6 wherein the flushing fluid is carbon dioxide.

9. The method of claim 6 wherein the flushing fluid includes blood.

10. The method of claim 6 wherein the flushing fluid is a substantially clear water based emulsion of a perflurocarbon.

11. The method of claim 6 wherein a flushing fluid is introduced intermittently.

12. The method of claim 1 wherein said medical procedure is the removal of a deposit at the site and the operative means includes a laser light transmitting fiber for directing laser irradiation at the site to remove at least a portion of the deposit.

13. The method of claim 1 wherein the operative means includes a viewing system and the method includes introducing a substantially clear flushing fluid into the blood vessel during at least part of the performance of the medical procedure.

14. The method of claim 13 wherein the flushing fluid is a substantially clear, physiologically compatible liquid bearing available oxygen.

15. The method of claim 13 wherein the medical procedure is the removal of a deposit at the site and the operative means includes a laser light transmitting fiber for directing laser irradiation at the site for a time period sufficient to remove at least a portion of the deposit.

16. The method of claim 1 wherein the medical procedure is removing tissue from the blood vessel site and the operative means includes tissue collecting means.

17. The method of claim 16 wherein the tissue collecting means includes a tube and wherein the medical procedure includes placing the end of the tube in contact with the tissue, introducing a negative pressure within the tube to grasp the tissue, and retracting the tube from the site to remove the tissue from the blood vessel.

18. The method of claim 1 wherein the oxygen bearing liquid is a water-based emulsion of a perfluorocarbon having an average particle size below about 0.2 micrometer.

19. The method of claim 1 wherein a plurality of oxygen bearing liquids is introduced in sequence.

20. A method of treating a site in a blood vessel with laser irradiation, the method comprising the steps of:
 (a) positioning within the blood vessel, proximate the site, the distal end of a conduit carrying a viewing system and means for emitting laser irradiation from the distal end of the conduit;
 (b) temporarily occluding the blood vessel upstream of the of the site;
 (c) introducing downstream of the produced occlusion and about the site a physiologically compatible liquid, from an external source, bearing sufficient available oxygen to maintain the viability of tissue downstream of the occlusion while the blood vessel is occluded;
 (d) positioning the distal end of the conduit adjacent the site such that the site can be viewed through the viewing system when the physiologically compatible oxygen bearing fluid is substantially clear; and
 (e) transmitting laser light through the conduit to subject the site with laser irradiation when the physiologically compatible oxygen bearing is sufficiently transparent to laser energy.

21. The method of claim 20 wherein the oxygen bearing liquid is introduced as a stream from a fluid passageway upstream of the site.

22. The method of claim 20 wherein the oxygen bearing liquid includes blood.

23. The method of claim 20 wherein the oxygen bearing liquid is a water based emulsion of a perfluorocarbon.

24. The method of claim 23 wherein the emulsion has an average particle size below about 0.2 micrometers.

25. The method of claim 20 wherein a substantially clear flushing fluid is introduced into the blood vessel downstream of the fluid occluding means for at least a portion of the performance of the medical procedure.

26. The method of claim 25 wherein the flushing fluid is saline.

27. The method of claim 25 wherein the flushing fluid is carbon dioxide.

28. The method of claim 25 wherein the flushing fluid includes blood.

29. The method of claim 25 wherein a flushing fluid is introduced intermittently.

30. The method of claim 20 wherein a plurality of oxygen bearing fluids is introduced in sequence.

* * * * *